United States Patent [19]

Webinger

[11] 4,270,692

[45] Jun. 2, 1981

[54] AIR DIFFUSER

[75] Inventor: George Webinger, Minneapolis, Minn.

[73] Assignee: Champion International Corporation, Stamford, Conn.

[21] Appl. No.: 112,922

[22] Filed: Jan. 17, 1980

[51] Int. Cl.³ .......................... B65D 5/38; B65D 13/06
[52] U.S. Cl. .......................................... 229/11; 229/8; 229/9
[58] Field of Search ..................... 229/8, 9, 10, 11, 19, 229/20; 206/806

[56] References Cited

U.S. PATENT DOCUMENTS

| | | | |
|---|---|---|---|
| 2,023,542 | 12/1935 | Peck | 206/806 X |
| 3,033,362 | 5/1962 | Marcalus | 206/806 X |
| 4,184,597 | 1/1980 | Gavin | 206/806 X |
| 4,219,145 | 8/1980 | Jaeschke | 229/8 |

Primary Examiner—Davis T. Moorhead
Attorney, Agent, or Firm—Evelyn M. Sommer

[57] ABSTRACT

Disclosed is a carton having adjustable air passages and a blank for forming it. The carton is formed of slidable inner and outer tapered sleeves having complementary spaced openings. The openings are positioned to provide open air passages when the inner sleeve is slid to a first position, and to close the passages as the inner sleeve is moved toward a second position. A stop is provided in the outer sleeve to limit movement of the inner sleeve when slid to the first position, while the taper between the sleeves precludes undue movement of the sleeves past the second position. A shiftable tab is also provided on the outer sleeve to block sliding movement of the sleeves relative to each other until the carton is ready for initial use.

17 Claims, 10 Drawing Figures

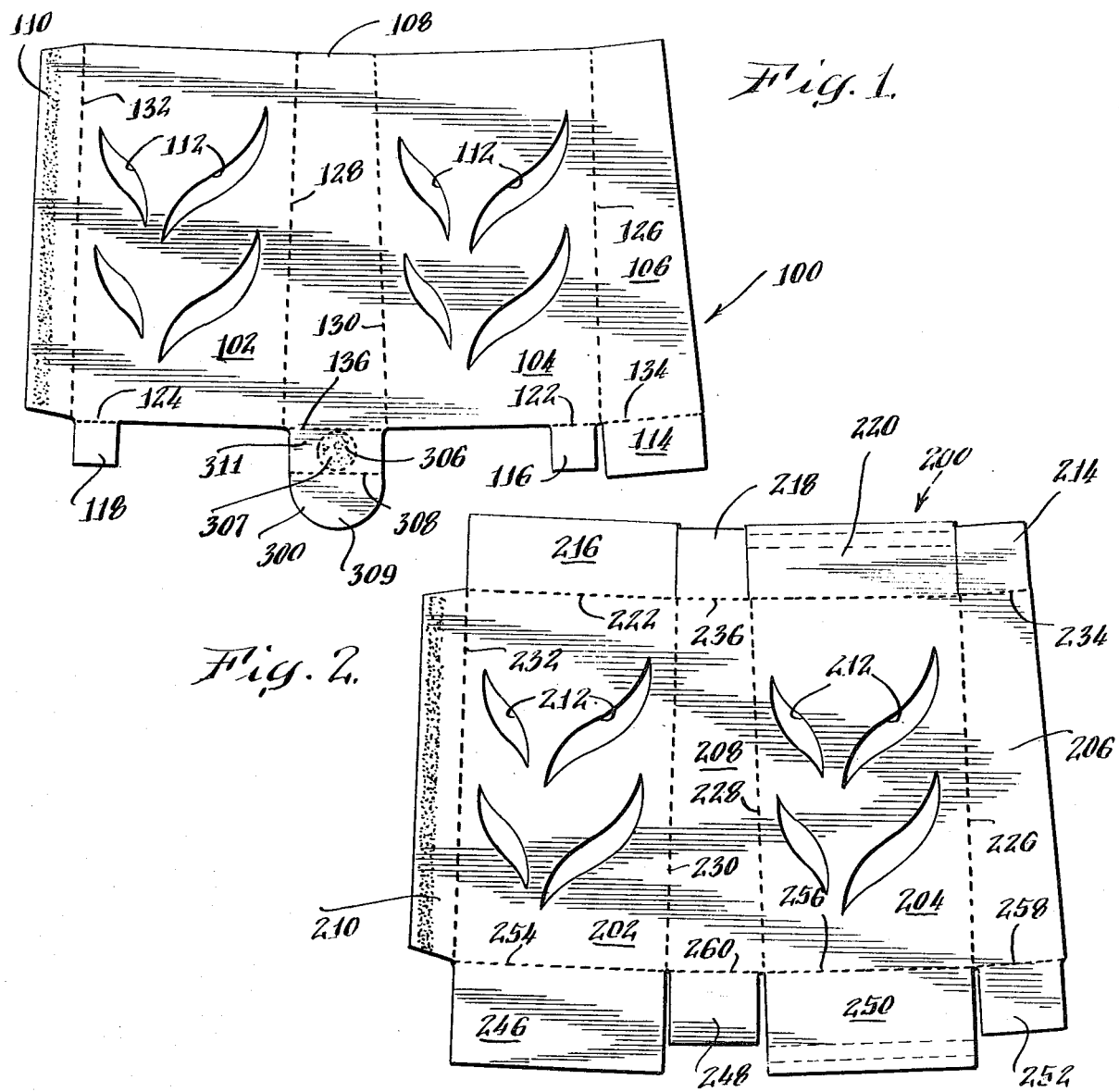
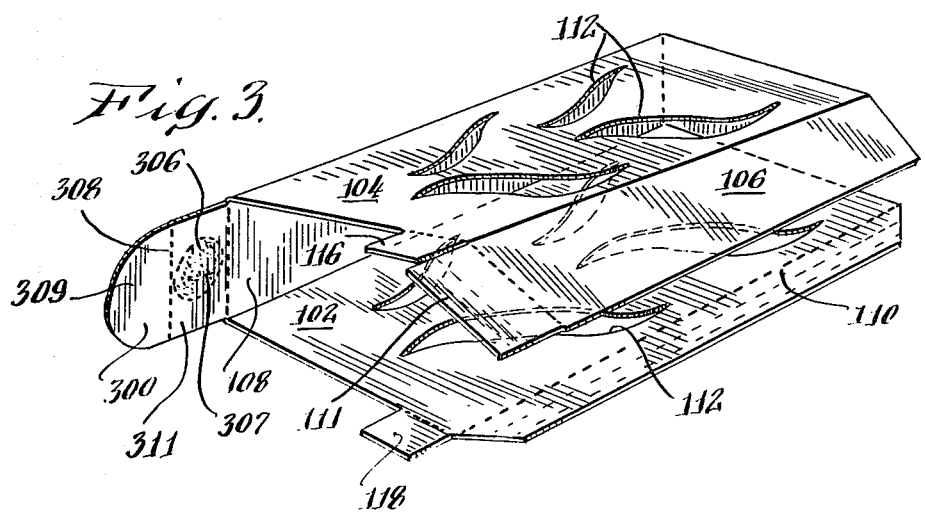

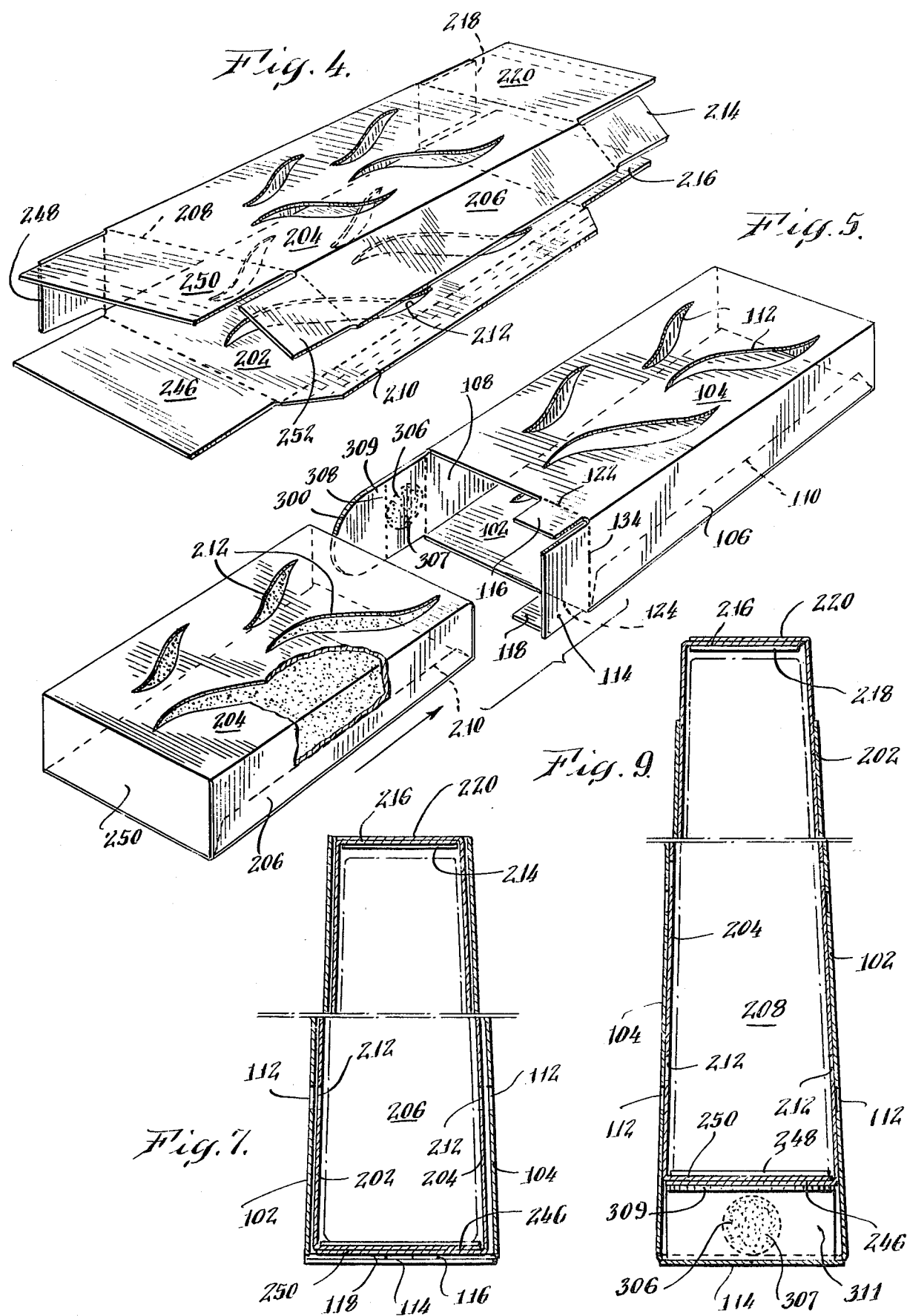

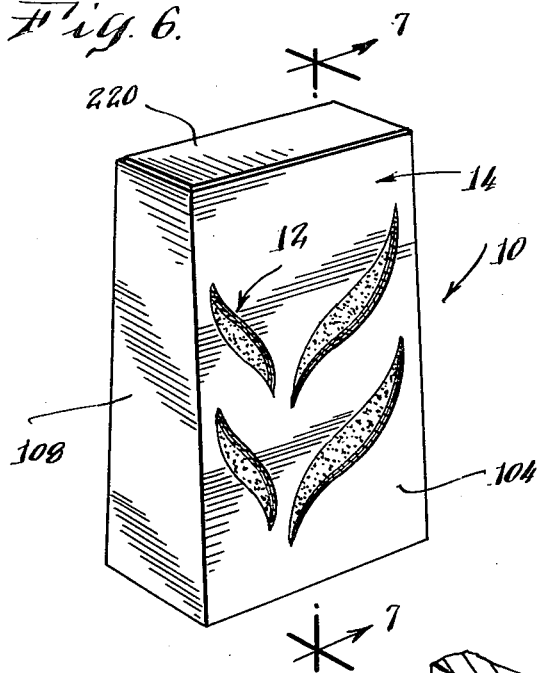
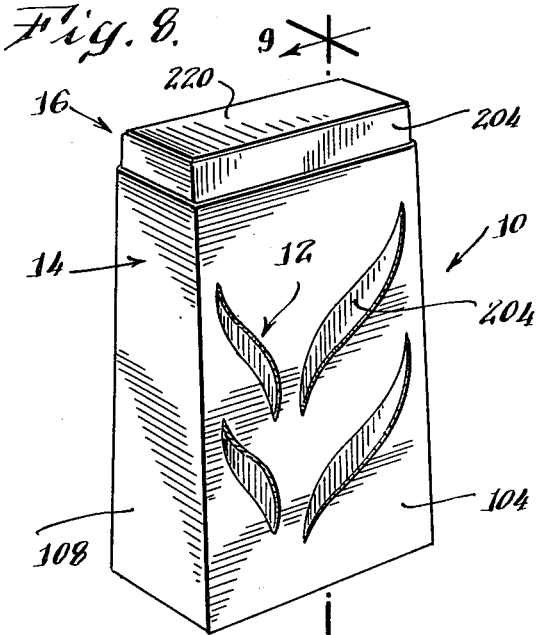
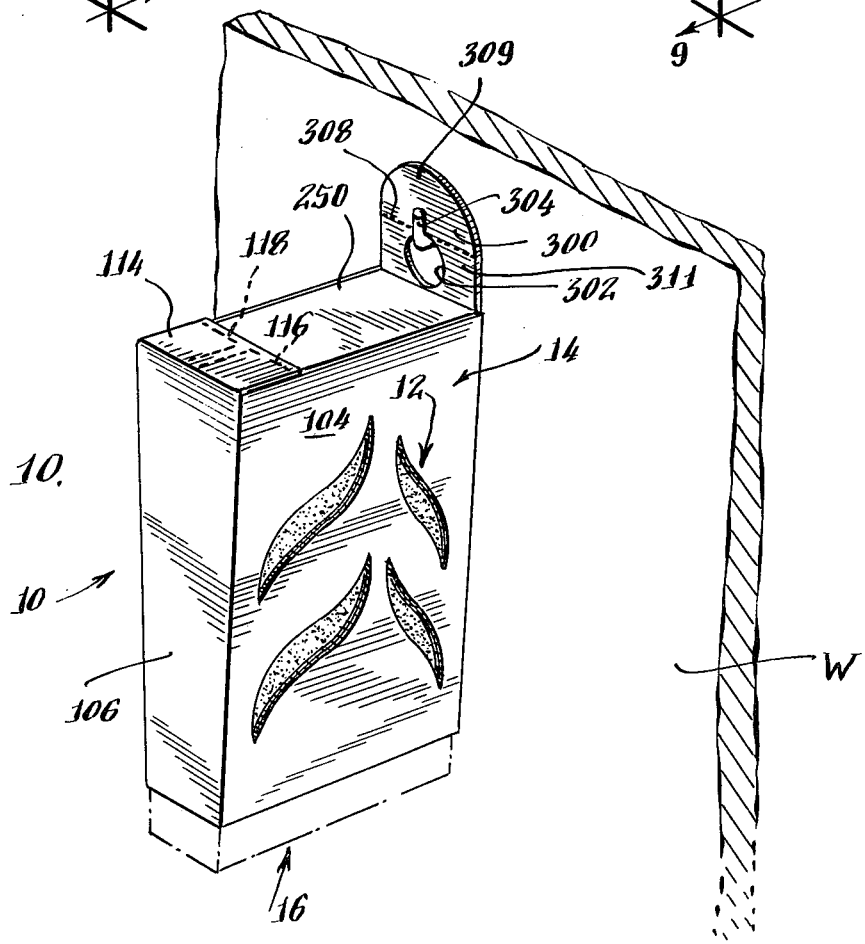

AIR DIFFUSER

BACKGROUND OF THE INVENTION

1. Field of Invention

The present invention relates to cartons, and more particularly to a carton for holding an active material and controllably releasing it to the air.

2. Description of the Prior Art

There are a variety of active materials for use in household and commercial applications which it is desirable to contact with and release into the ambient air. Among these are insecticides and air fresheners which can be packaged in solid form in containers having air passages which permit release. Frequently, products of this type are packaged in containers having a plurality of openings which are closed at the time of purchase but which are opened at the time of use to allow room air to circulate over the surface of the solid active material.

In one type of carton, the openings are covered with a panel of release paper. When the consumer is ready to use the product, such as an air freshener, the release paper is peeled from the face of the container to allow room air to begin circulating through the openings. In another type of carton, the consumer activates the air freshener material by squeezing to release an encapsulated active ingredient. In yet another type of carton, holes in an outer wall are opened or closed by a slidable inner sheet which acts as a valve.

Molded plastic containers, usually consisting of a molded shell and a separate molded cover, have been employed to hold air freshener material. However, while molded plastic containers have an aesthetically pleasing appearance, the cost of making them is higher than might be desired. The shell and cover must be moled in separate operations and stored in unassembled form until the air freshener insert is loaded. The cover then must be glued or otherwise secured to the shell to provide a closed container. The extra time required for the separate manufacturing and assembly operations results in added manufacturing costs for the package and ultimately for the product sold therein. The fact that the molded shells and covers must be shipped and stored in their molded form will also cause increased transportation and storage costs.

In a prior patent application, U.S. Ser. No. 25,012 filed Mar. 29, 1979 now U.S. Pat. No. 4,219,145 entitled "CARTON WITH ADJUSTABLE AIR PASSAGES", assigned to the same assignee as the present invention, an improved package for controllably releasing active materials to the air is disclosed which has inner and outer slidable members constructed of a sheet material wherein the inner and outer members can be slidably moved between open and closed positions. The carton has a plurality of adjustable air passages and comprises: (a) a first tapered sleeve forming an outer carton unit, said first sleeve being closed at at least one end and having a plurality of spaced openings therein; and (b) a second tapered sleeve forming an inner carton unit, said second sleeve being nested within said first sleeve and being slidable between a first position and a second position, said second sleeve being closed at at least the end opposite said end closed in said first sleeve and having a plurality of spaced openings therein arranged complementarily to said spaced openings in said outer carton unit to align with the openings therein when said inner carton unit is in said first position, and to align with the spaces between said openings in said outer carton unit when said inner carton unit is in said second position.

SUMMARY OF THE INVENTION

The present invention relates to an improved package of the type having an inner and outer tapered carton unit provided with complementary openings, which when aligned permit the release or diffusion of material housed within the inner unit to the air. The tapered sleeves normally bind when moved relative to each other when the openings are out of alignment, to maintain the closure, when the diffuser is inoperative. However, movement in the opposite direction causes the openings in the inner and outer sleeves to be readily and easily aligned.

The package of the present invention employs a stop on the outwardly tapering end of the outer carton sleeve to restrict movement of the inner carton sleeve when the air diffuser openings are aligned. Additionally, a shiftable, removably mounted blocking tab formed integral with the opposed edge of the outer sleeve is disposed inside the outer sleeve in blocking relationship to the inner sleeve to prevent relative movement between the sleeves until the package is ready for initial use. A scored, adhesive tear dot in the blocking tab secures the blocking tab to an interior side wall of the outer sleeve; the end of the blocking tab is grasped and pulled by a user to withdraw such tab from the outer sleeve, thereby freeing the inner sleeve for sliding movement within the outer sleeve.

BRIEF DESCRIPTION OF THE DRAWINGS

The invention will be better understood and its advantages will be more apparent from the following detailed description, especially when read in light of the attached drawings wherein:

FIGS. 1 and 2 are plan views of the blanks for forming the outer and inner carton sleeves, respectively, of the carton of the present invention;

FIGS. 3 and 4 are perspective views illustrating the initial stages of folding of the blanks shown in FIGS. 1 and 2, respectively;

FIG. 5 is a perspective view illustrating the final assembly of the composite carton of the present invention;

FIG. 6 is a perspective view of the assembled carton of the present invention showing the air passages in their operative, open position;

FIG. 7 is a cross-sectional view taken along line 7—7 in FIG. 6;

FIG. 8 shows the carton shown in FIG. 6 with the openings in their inoperative, closed position;

FIG. 9 is a cross-sectional view taken along line 9—9 in FIG. 8; and

FIG. 10 is a perspective view of the assembled carton of the present invention mounted on a support hook and illustrating its optical manner of use when so supported.

DETAILED DESCRIPTION OF THE PREFERRED EMBODIMENT

The present invention provides a two component carton having adjustable air passages and a blank for forming it. The carton is especially adapted for use in storing a solid active material such as an insecticide or a room air freshener during transportation and display, and then functioning as a dispenser for the active material by controllably releasing the active material to ambient air through adjustable air passages during use. The carton is formed of slidable inner and outer tapered sleeves having complementary, spaced openings. The openings are positioned to permit room air to circulate into contact with the active material and back to the room in their open position and to also permit their partial or complete closure as the sleeves are moved to a second, closed position.

The carton 10 in FIGS. 6-10, inclusive, is a presently preferred embodiment according to this invention. The carton 10 can be supported by means such as a tab 300 having a opening 302, hung from a hook 304 mounted on a vertical support wall W. Alternatively, the carton 10 can be free standing, as illustrated in FIGS. 6 and 8, supported on a rectangular base, in which case the tab is torn away from the carton and discarded.

The carton 10 has a substantially rectangular cross-section at any point perpendicular to the vertical axis. While this embodiment is preferred, it is to be understood that the carton can have other cross-sectional shapes perpendicular to the axis along which it slides. For example, it is possible to have virtually any cross-section such as triangular, square, pentagonal, hexagonal, octangonal, and the like. The objects of the present invention are equally well attained despite the particular cross-section, and can be attained even with circular and oval cross-sections.

With this general explanation, the following detail will be directed toward a preferred embodiment of the invention which is particularly well suited for use in dispensing air fresheners which are held in solid form within the carton 10.

Referring now to FIGS. 6, 8 and 10, carton 10 is shown in FIGS. 8 and 10 (in phantom lines) in the closed position and is shown in FIGS. 6 and 10 (face line position) in the fully open position. It will be understood that the openings 12 can be adjusted to any degree between the first position wherein they are completely open and the second position wherein they are completely closed. Adjustment between the open and the closed positions is obtained by moving outer carton unit 14 relative to inner carton unit 16 to obtain the desired degree of alignment and therefore opening of the apertures in the inner carton 16 and outer carton unit 14. The openings 12 are shown on the front and back panels, but this is preferred only. The openings can be positioned as desired.

The detail of the construction of the preferred embodiment will be better understood by viewing FIGS. 1 through 5 which show the various stages of construction of the carton 10. FIG. 1 shows an outer blank 100 for forming the outer carton unit 14 and FIG. 2 shows an inner blank 200 for forming the inner carton unit 16.

FIG. 1 shows outer blank 100 for forming the outer carton unit 14. This blank 100 is being viewed from what will be its outside surface. As will be seen in FIG. 3, the blank 100 can rest on back panel 102 for assembly by folding the other panels upwardly from the horizontal to the final form. The blank comprises rectangular front panel 104, rectangular rear panel 102, and trapezoidal side wall panels 106 and 108. These parts are of essentially the same dimensions as those of the like parts of the inner carton blank 200. If desired, to obtain a better sliding engagement, the outer and inner carton units 14 and 16 can differ in overall dimension by about 1 to 2 times the thickness of the sheet material for forming the cartons. The sheet materials used in forming the carton can be any of those typically employed for making disposable cartons. Preferably, a paperboard material or a laminate of a paperboard with a plastic material will be employed.

Referring again to FIG. 3, the outer carton blank 100 also has a glue flap 110 as well as flaps 114, 116 and 118 for closing one end of the outer carton unit 14. Flaps 116 and 118 are hingedly connected to the bottom edge of front panel 104 and back panel 102, respectively, while flap 114 is hingedly connected to bottom edge 134 of trapezoidal side panel 106. The tab 300 is hingedly connected to bottom edge 136 of trapezoidal side panel 108 and includes scored tear out dot or circle 306 which may form opening 302. The inner face of tear out dot 306 has an adhesive 307 preapplied thereto for purposes which will become later apparent. Tab 300 is bendable 180 degrees inwardly along a score line 136 into overlapping face-to-face contact with side wall panel 108. Score line 308 divides the tab 300 into an intermediate stretch or section 311 and a free outer extremity or section 309. Apertures or openings 112 are provided in spaced relation on both the front and the back panels. The openings are arranged such that in the final construction they will be complementary to similar spaced openings 212 in the inner carton unit 16 to align with the openings 212 therein when said inner carton unit 16 is in the first or open position (as shown in FIG. 6), and to align with the spaces between the openings 112 in the outer carton unit 14 when the inner carton unit 16 is in the second or closed position (as shown in FIG. 8).

It is preferred that the openings 112 be of essentially the same shape and size as the openings 212 in the inner carton blank 200. Because it is desired in the preferred embodiment of the invention to enable the complete closing of the openings, the space between the openings 112 on the outer carton blank 100, as measured along any line parallel to the vertical axis of the final carton 10, must be of greater vertical extent than the openings 112 themselves. The openings 212 in the inner carton blank 200 must be similarly positioned and spaced so that alignment with openings 112 in the constructed carton 10 will be facilitated.

In assembling the outer carton unit 14 from the blank 100, panels 102, 104, 106, 108 and glue flap 110 are folded about fold lines 126, 128, 130 and 132 as shown in FIG. 3. The blank 100 is then glued in folded position by securing flue flap 110 of the interior of side panel 106. The flaps 116 and 118 are then folded 90 degrees relative to the bottom edges of panels 104 and 102, respectively, and adhesively secured to the lower surface of flap 114 to form a stop to limit movement of the inner carton unit 16 by abutment with the closed lower end of inner carton unit 16. If used in its free standing mode (FIGS. 6 and 8), tab 300 may be torn along bottom edge 136 and removed entirely; bottom edge 136 may be scored if desired to facilitate such tearing.

The inner blank 200 is shown in FIG. 2 and comprises a rectangular back panel 202, a rectangular front panel 204 and two trapezoidal side panels 206 and 208. As will be seen in FIG. 4, the blank 200 can rest on back panel 202 with the other carton panels being folded up from the horizontal to the final form. A glue tab 210 is provided for sealing the inner blank 200 into a sleeve by connecting to the interior of side panel 206. The inner blank 200 has a substantially rectangular cross-section after folding as shown in FIG. 4. Both the front panel 204 and the rear panel 202 have spaced openings 212 therein.

After insertion of the product, the inner carton unit 16 is closed at both ends. The top end has flaps 214, 216, 218 and 220 which are folded over and adhesively connected to form a closed end. Flap 216 is bendable from back panel 202 about a fold line 222. Similarly, flap 220 can be bent from front panel 204 about fold line 224, while flaps 214 and 218 are bendable about fold lines 234 and 236, respectively. The bottom end has flaps 246, 248, 250 and 252 which are similarly folded over about fold lines 254, 260, 256 and 258, respectively and adhesively connected to form a second closed end.

Referring to FIG. 4, the sequence of construction of the inner carton unit 16 can be seen more clearly where the panels 202, 206, 204, 208 and glue flap 210 are folded about intermittent score lines 226, 228, 230 and 232. Then, glue flap 210 is adhered to wall 206. Tabs 214 and 218 are folded about fold lines 234 and 236 and then overlayed by upper tabs 216 and 220 which are folded about fold lines 222 and 224, respectively. Tabs 216 and 220 are preferably adhesively secured in known manner. Similarly, tabs 248 and 252 are folded about fold lines 260 and 258 and then overlayed by tabs 246 and 250, folded about lines 254 and 256 and adhesively joined.

Referring now to FIGS. 5 and 7, there is shown the next stage in construction of the carton wherein the inner carton unit 16 in fully constructed form is slidably passed into partially assembled outer carton unit 14. After insertion of inner carton unit 16 into outer carton unit 14, flaps 114, 116 and 118 are folded about fold lines 134, 122 and 124 to provide a stop on the bottom end of the outer carton unit 14 to preclude excessive movement of the inner carton relative to the outer carton towards the outwardly tapered or flared end of carton 10. Then, tab 300 is folded inwardly 180 degrees along score line 136 into face-to-face engagement with the inside face of side wall panel 108 and is adhered to the latter by virtue of adhesive 307 on tear out dot 306. Simultaneous with the folding of tab 300 about score line 136, the outer free extremity of tab 300 engages the bottom flap 250 of innercarton 16 and is forced to fold 90 degrees into flush contact with bottom flap 250 and is disposed essentially perpendicular to the side wall panel 108. The outer free extremity of tab 300 is thus disposed in blocking engagement with the inner carton unit 16 and maintains the latter in its closed position until the package is ready for use. Tab 300 is held in blocking relationship to the inner carton unit by the adhesive 307 which holds the intermediate stretch of tab 300 essentially parallel to side wall panel 108.

The tapered side panels promote tight frictional engagement of the inner and outer carton units in intermediate relative positions, to selectively adjust the width of the complementary openings. The tapered side panels preclude complete disassociation of the inner and outer carton units in one direction of movement by wedging engagement. The tight friction fit produced by the tapered side walls serves to prevent or at least substantially reduce air flow between the interior of the package and the atmosphere when the package is closed, thereby preventing sublimation of the product during periods of non-use. The primary and most important purpose of tab 300 is to initially hold the inner carton unit in its raised, closed position (FIG. 8) in order to prevent inadvertant opening and activation of the package prior to use thereof by a consumer, as might occur during shipping for example. When the package is about to be used, the consumer merely grasps the free outer extremity 309 of the tab 300 and pulls the tab 300 outwardly from the interior of the outer carton unit 14. Upon pulling of the tab 300, the intermediate stretch 311 tears around the perforated score lines defining tear out dot 306, leaving tear out dot adhered to the side wall panel 108 and forming the opening 302 in tab 300. At this point, the inner carton unit 16 may slide downwardly within outer carton unit 16 to open and thereby activate the package. The tab 300 may then be removed by tearing the same along bottom edge 136, or, if desired the tab 300 can remain on the package and be employed to hang the same from the hook 304, as discussed previously. In any event the stop panels on the outer carton unit 16 preclude disassociation of inner and outer carton units once the tab 300 is pulled from its blocking position.

What is claimed as new is:

1. A carton having a plurality of adjustable air passages comprising:
   (a) a first tapered sleeve forming an outer carton unit, said first sleeve having a plurality of spaced openings therein and a plurality of panels forming a stop;
   (b) a second tapered sleeve forming an inner carton unit, said second sleeve being nested within said first sleeve and being slidable between a first position and a second position, said second sleeve being closed at opposite ends and having a plurality of spaced openings therein arranged complementary to said spaced openings in said outer carton unit to align with the openings therein when said inner carton unit is in said first position in abutment with the stop in said first sleeve, and to align with the spaces between said openings in said outer carton unit when said inner carton unit is in said second position; and
   (c) means shiftably mounted on at least one of said first and second tapered sleeves for selectively blocking sliding movement of said second tapered sleeve from said second position thereof to said first position thereof.

2. A carton as defined in claim 1 wherein the first and second sleeves are of substantially the same shape and dimension.

3. A carton as defined in claim 1 wherein both the first and second sleeves are constructed of paperboard.

4. A carton as defined in claim 1 wherein the first and second sleeves slide along a vertical axis and have rectangular cross-sections perpendicular to the vertical axis.

5. A carton as defined in claim 1 wherein the openings in the first and second sleeves are of substantially the same size and dimension.

6. A carton as defined in claim 1 wherein the first and second sleeves slide along a vertical axis and the openings in each are spaced vertically by a distance at least equal to the vertical dimension of the openings along a line parallel to the vertical axis.

7. A carton as defined in claim 1 wherein the first and second sleeves slide along a vertical axis and the lower end of the carton is larger than the upper end thereof.

8. A carton as defined in claim 7 wherein said first sleeve, forming said outer carton unit, has said stop at its bottom end and is open at its top end.

9. A carton as defined in claim 8 wherein said first and second sleeves have substantially rectangular cross-sections perpendicular to the vertical axis.

10. A carton as defined in claim 9 wherein said closed ends of said second sleeve are each formed by an opposed pair of flaps, each secured to the tops of two opposed side walls by fold lines.

11. A carton as defined in claim 10 wherein the first and second sleeves both have substantially rectangular front and back panels and trapezoidal side panels.

12. A two part blank for forming the carton as described in claim 1.

13. A carton as defined in claim 1 wherein said means for blocking sliding movement of said second tapered sleeve comprises a tab hingedly connected to an edge of said first tapered sleeve.

14. A carton as defined in claim 13 wherein said tab includes a score line therein defining a removable tear out portion for forming an opening in said tab, said tear out portion having an adhesive applied thereto.

15. A carton as defined in claim 13 wherein said tab includes a score line in a midsection thereof dividing said tab into an intermediate section and an extremity section, said intermediate section being disposed in face-to-face relationship to inside surfaces of said first tapered sleeve, said extremity section extending angularly away from said intermediate section and into engagement with one end of said second tapered sleeve.

16. A carton as defined in claim 15, wherein said extremity section extends essentially perpendicular to said intermediate section and said intermediate section is disposed in face-to-face engagement with said one end of said second tapered sleeve.

17. A carton as defined in claim 16, wherein said intermediate section is adhesively secured to said inside surfaces of said first tapered sleeve.

* * * * *